US00PP15602P2

(12) United States Plant Patent
Hanes

(10) Patent No.: US PP15,602 P2
(45) Date of Patent: Mar. 1, 2005

(54) ***VERBENA* PLANT NAMED 'LAN CHERED'**

(50) Latin Name: *Verbena hybrida*
Varietal Denomination: Lan Chered

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/818,500

(22) Filed: Apr. 5, 2004

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—C. A. Whealy

(57) ABSTRACT

A new and distinct cultivar of *Verbena* plant named 'Lan Chered', characterized by its compact, low and outwardly spreading, and decumbent plant habit; freely branching habit; early and uniform flowering habit and dark cherry red-colored flowers.

1 Drawing Sheet

Botanical classification/cultivar designation: *Verbena hybrida* cultivar Lan Chered.

BACKGROUND OF THE INVENTION

The present Invention relates to a new and distinct cultivar of *Verbena* plant, botanically known as *Verbena hybrida,* and hereinafter referred to by the name 'Lan Chered'.

The new *Verbena* is a product of a planned breeding program conducted by the Inventor in Gilroy, Calif. The objective of the breeding program is to develop new compact *Verbena* cultivars with early and uniform flowering, good basal branching, attractive flower and foliage coloration, and tolerance to Powdery Mildew.

The new *Verbena* originated from a cross-pollination made by the Inventor in June, 2001 of a proprietary *Verbena hybrida* selection identified as code number 00-1276-2, not patented, as the female, or seed, parent with a proprietary *Verbena hybrida* selection identified as code number 00-1252-4, not patented, as the male, or pollen, parent. The cultivar Lan Chered was discovered and selected by the Inventor as a flowering plant within the progeny from this cross-pollination in a controlled environment in Gilroy, Calif. in January, 2002.

Asexual reproduction of the new cultivar by terminal cuttings in Gilroy, Calif., since January, 2002 has shown that the unique features of this new *Verbena* are stable and reproduced true to type in successive generations of asexual reproduction.

SUMMARY OF THE INVENTION

The following traits have been repeatedly observed and are determined to be the unique characteristics of 'Lan Chered'. These characteristics in combination distinguish 'Lan Chered' as a new and distinct cultivar:

1. Compact, low and outwardly spreading, and decumbent plant habit.
2. Freely branching habit.
3. Early and uniform flowering habit.
4. Dark cherry red purple-colored flowers.
5. Relatively less susceptible to Powdery Mildew.

In side-by-side comparisons conducted in Gilroy, Calif., plants of the new *Verbena* differed from plants of the female parent selection in the following characteristics:

1. Plants of the new *Verbena* were more vigorous than plants of the female parent selection.
2. Plants of the new *Verbena* and the female parent selection differed in flower color as plants of the female parent selection had light peach-colored flowers.

In side-by-side comparisons conducted in Gilroy, Calif., plants of the new *Verbena* differed from plants of the male parent selection in the following characteristics:

1. Plants of the new *Verbena* were slightly more compact than plants of the male parent selection.
2. Plants of the new *Verbena* and the male parent selection differed in flower color as plants of the male parent selection had dark purple-colored flowers.

The new *Verbena* can be compared to the cultivar, Scarlena, disclosed in U.S. Plant Pat. No. 12,578. However, in side-by-side comparisons conducted in Gilroy, Calif., plants of the new *Verbena* differed from plants of the cultivar Scarlena in the following characteristics:

1. Plants of the new *Verbena* were slightly more upright than plants of the cultivar Scarlena.
2. Plants of the new *Verbena* were more freely branching than plants of the cultivar Scarlena.
3. Leaves of plants of the new *Verbena* were darker in color than leaves of plants of the cultivar Scarlena.
4. Plants of the new *Verbena* and the cultivar Scarlena differed in flower color as plants of the cultivar Scarlena had bright scarlet red-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Lan Chered'.

The photograph at the bottom of the sheet is a close-up view of typical flower racemes and leaves of 'Lan Chered'.

Flower and foliage colors in the photographs may differ slightly from the color values cited in the detailed botanical description which accurately describe the colors of the new *Verbena*.

DETAILED BOTANICAL DESCRIPTION

Plants of the cultivar Lan Chered have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures about 24 to 32° C., night temperatures about 13 to 18° C. and light levels about 2,000 foot-candles. Plants used for the photographs and description were about twelve weeks from planting rooted cuttings and were pinched twice. In the following description, color references are made to The Royal Horticultural Society Colour Chart, 1995 Edition, except where general terms of ordinary dictionary significance are used.

Botanical classification: *Verbena hybrida* cultivar Lan Chered.

Parentage:

*Female, or seed, parent.*—Proprietary *Verbena hybrida* selection identified as code number 00-1276-2, not patented.

*Male, or pollen, parent.*—Proprietary *Verbena hybrida* selection identified as code number 00-1252-4, not patented.

Propagation:

*Type cutting.*—Terminal cuttings.

*Time to initiate roots.*—About 7 to 10 days at 22 to 24° C.

*Time to produce a rooted cutting or liner.*—About three to four weeks at 22 to 24° C.

*Root description.*—Fine, fibrous; white in color.

*Rooingt habit.*—Freely branching.

Plant description:

*Form.*—Compact, low and outwardly spreading, and decumbent plant habit.

*Growth and branching habit.*—Vigorous and freely-branching with about eight main stems and multiple secondary lateral branches.

*Plant height.*—About 12 cm.

*Plant diameter or spread.*—About 55 cm.

*Lateral branches.*—Length: About 33 cm. Diameter: About 2.5 mm. Internode length: Vegetative branches, about 2.5 cm; reproductive branches, about 4.8 cm. Strength: Strong. Texture: Pubescent. Color: 144A.

*Foliage description.*—Arrangement: Opposite, simple. Length: About 4 cm. Width: About 2.8 cm. Shape: Deltoid. Apex: Broadly acute. Base: Attenuate. Margin: Crenate. Texture, upper and lower surfaces: Coarse, pubescent. Venation pattern: Pinnate, netted.

*Color.*—Developing and fully expanded foliage, upper surface: 147A. Developing and fully expanded foliage, lower surface: 147B. Venation, upper surface: 147B. Venation, lower surface: 147C.

*Petiole.*—Length: About 1 cm. Diameter: About 2 mm. Color: 147C.

Flower description:

*Flower type and habit.*—Single upright salverform flowers arranged on terminal racemes; flowers sessile. Freely flowering with about 20 flowers per raceme; about three racemes per lateral branch. Inflorescences positioned above and beyond the foliage. Flowers last about five to seven days under greenhouse conditions. Flowers not persistent.

*Fragrance.*—None detected.

*Flowering season.*—In the garden, flowering is continuous from spring until fall.

*Inflorescence size.*—Height: About 3 cm. Diameter: About 5.3 cm.

*Flower size.*—Diameter: About 1.8 cm. Tube length: About 2.6 cm.

*Flower buds.*—Length: About 1.4 cm. Diameter: About 3 mm. Shape: Tubular. Color: 60B.

*Petals.*—Quantity/arrangement: Five per flower fused at base. Lobe length: About 8 mm. Lobe width: About 7 mm. Shape: Cordate. Apex: Emarginate. Margin: Entire. Texture, upper and lower surfaces: Velvety, smooth. Color: When opening, upper surface: 46B. When opening, lower surface: 54A to 54B. Fully opened, upper surface: More red than 57A; towards the center, 46B; color becoming closer to 57C with development. Fully opened, lower surface: 57D. Throat: Close to 154D.

*Sepals.*—Quantity/arrangement: Five, fused into a tube. Length: About 1.2 cm. Diameter: Less than 1 mm. Shape: Ligulate. Apex: Acuminate. Margin: Entire. Texture, upper and lower surfaces: Coarse, pubescent. Color, upper surface: 147B. Color, lower surface: 147C.

*Peduncles.*—Length: About 6.5 cm. Diameter: About 1 mm. Angle: Upright or curving upward on horizontal stems. Strength: Strong. Color: 144A.

*Reproductive organs.*—Stamens: Quantity: Four. Anther shape: Ovoid. Anther length: Less than 1 mm. Anther color: 145A. Pollen amount: Scarce. Pollen color: 150B. Pistils: Quantity: One. Pistil length: About 2 cm. Stigma shape: Bi-parted. Stigma color: 145A. Style length: About 1.8 cm. Style color: 145D. Ovary color: 145B.

*Fruit/seed.*—Fruit and seed production has not been observed.

Disease/pest resistance: Plants of the new *Verbena* have been observed to be relatively less susceptible to Powdery Mildew. Plants of the new *Verbena* have not been observed to be resistant to other pathogens and pests common to *Verbena*.

Temperature tolerance: Plants of the new *Verbena* have been observed to be tolerant to temperatures ranging from 2 to 40° C.

It is claimed:

1. A new and distinct cultivar of *Verbena* plant named 'Lan Chered', as illustrated and described.

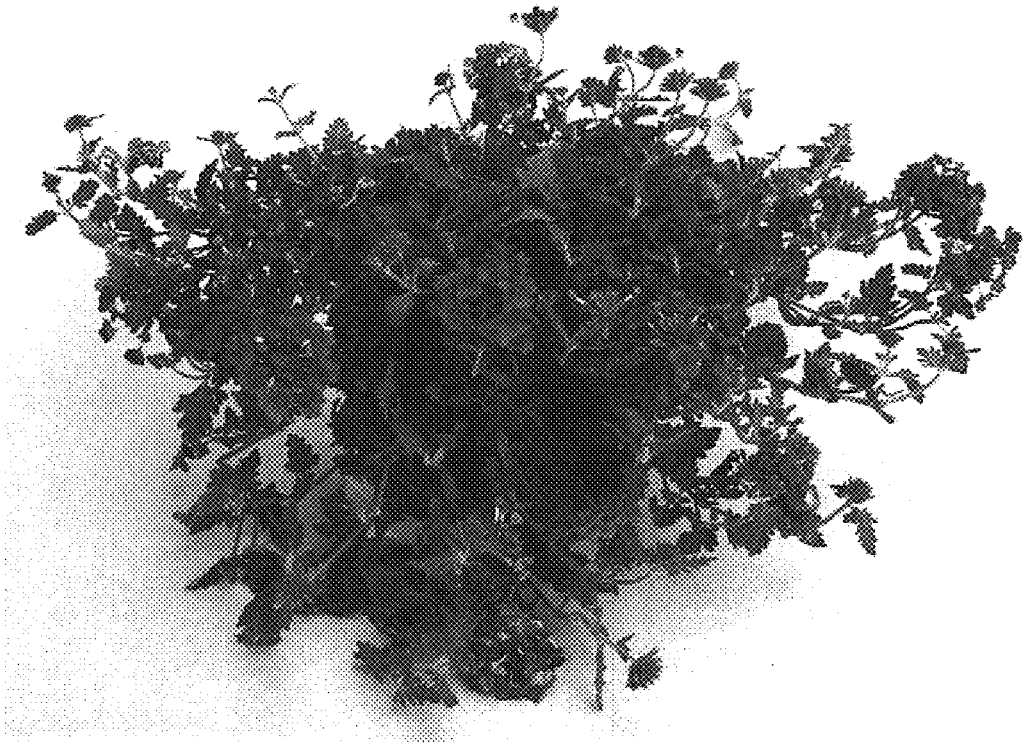
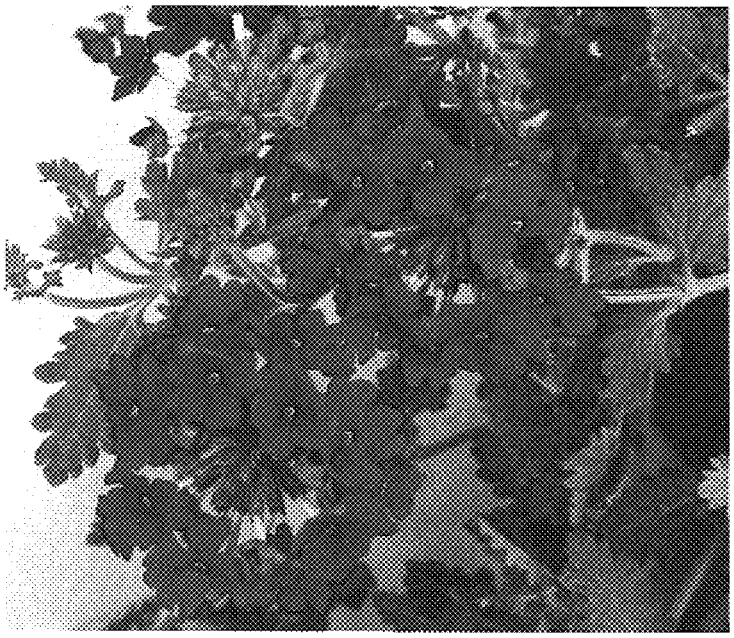

* * * * *